United States Patent
Robinson

(10) Patent No.: US 10,159,512 B2
(45) Date of Patent: Dec. 25, 2018

(54) HALLUX ABDUCTO VALGUS ASSEMBLIES

(75) Inventor: Dror Robinson, Kfar Shmuel (IL)

(73) Assignee: Bonfix Ltd, Jerusalem (IL)

( * ) Notice: Subject to any disclaimer, the term of this patent is extended or adjusted under 35 U.S.C. 154(b) by 634 days.

(21) Appl. No.: 13/257,301

(22) PCT Filed: Mar. 17, 2010

(86) PCT No.: PCT/IB2010/051155
§ 371 (c)(1),
(2), (4) Date: Sep. 18, 2011

(87) PCT Pub. No.: WO2010/106507
PCT Pub. Date: Sep. 23, 2010

(65) Prior Publication Data
US 2012/0016426 A1    Jan. 19, 2012

Related U.S. Application Data

(60) Provisional application No. 61/160,736, filed on Mar. 17, 2009.

(51) Int. Cl.
*A61B 17/68* (2006.01)
*A61B 17/84* (2006.01)
(Continued)

(52) U.S. Cl.
CPC ............ *A61B 17/68* (2013.01); *A61B 17/842* (2013.01); *A61B 17/864* (2013.01); *A61B 17/8085* (2013.01); *A61B 2017/565* (2013.01)

(58) Field of Classification Search
CPC . A61B 17/842; A61B 17/8085; A61B 17/864; A61B 2017/565; A61B 2017/564; A61B 17/0466; A61B 17/0401
(Continued)

(56) References Cited

U.S. PATENT DOCUMENTS 1,055,810 A * 3/1913 Scholl ................... A61F 5/019
602/30
2,596,038 A * 5/1952 Mayer ................... A61F 5/019
602/30
(Continued)

FOREIGN PATENT DOCUMENTS

BE    1 010 569    10/1998
EP    0760231    8/1996
(Continued)

OTHER PUBLICATIONS

Arthrex, Inc.. "Comprehensive Solutions for Forefoot and Midfoot Surgery using the Mini TightRope® System." Arthrex Product Brochure (2008). Last accessed Apr. 16, 2014. <http://podiatry.com/images/eZines/RI/0910/44/MiniTightRope.pdf>.*
(Continued)

*Primary Examiner* — Kevin T Truong
*Assistant Examiner* — Marcela I Shirsat
(74) *Attorney, Agent, or Firm* — Mark S. Cohen; Pearl Cohen Zedek Latzer Baratz LLP

(57) ABSTRACT

Disclosed is an assembly for in vivo alignment of two or more bones in a living body. The assembly comprises a cannulated sleeve (132) configured to secure in a bore (133) in a first bone, a mesh body (136) having a proximal arm configured to be engaged by the cannulated sleeve, and a distal arm configured to be secured to a portion of a second bone. The assembly further includes a fastener (138) configured to secure the distal arm to the portion of the second bone.

5 Claims, 12 Drawing Sheets

(51) Int. Cl.
*A61B 17/86* (2006.01)
*A61B 17/80* (2006.01)
*A61B 17/56* (2006.01)

(58) Field of Classification Search
USPC ..... 606/328, 60, 86 R, 90, 99, 96, 103–105, 606/148, 232, 228; 602/5, 23, 30–32, 36, 602/37, 60–61, 65, 66; 623/21.15
See application file for complete search history.

(56) References Cited

U.S. PATENT DOCUMENTS

| | | | |
|---|---|---|---|
| 4,159,716 A | | 7/1979 | Borders |
| 5,250,049 A | * | 10/1993 | Michael ............... 606/324 |
| 5,433,665 A | | 7/1995 | Beaty et al. |
| 5,507,812 A | | 4/1996 | Moore |
| 5,529,075 A | * | 6/1996 | Clark ............... 128/898 |
| 5,575,819 A | * | 11/1996 | Amis ............... 623/13.13 |
| 5,800,543 A | * | 9/1998 | McLeod et al. ........ 623/13.2 |
| 5,941,885 A | | 8/1999 | Jackson |
| 6,629,943 B1 | * | 10/2003 | Schroder ............... 602/30 |
| 7,875,058 B2 | | 1/2011 | Holmes, Jr. |
| 8,696,719 B2 | | 4/2014 | Lofthouse et al. |
| 8,828,067 B2 | | 9/2014 | Tipirneni et al. |
| 2002/0123750 A1 | * | 9/2002 | Eisermann ......... A61B 17/68 606/285 |
| 2003/0114857 A1 | | 6/2003 | Carchidi et al. |
| 2003/0236555 A1 | * | 12/2003 | Thornes ............... 606/232 |
| 2004/0138683 A1 | * | 7/2004 | Shelton ............ A61B 17/0401 606/151 |
| 2005/0065533 A1 | | 3/2005 | Magen et al. |
| 2005/0070906 A1 | | 3/2005 | Clark et al. |
| 2005/0149032 A1 | | 7/2005 | Vaughen et al. |
| 2005/0240188 A1 | | 10/2005 | Chow et al. |
| 2006/0241608 A1 | * | 10/2006 | Myerson et al. ............... 606/69 |
| 2007/0010818 A1 | * | 1/2007 | Stone ............... A61B 17/683 606/331 |
| 2007/0161991 A1 | | 7/2007 | Altaric et al. |
| 2007/0185489 A1 | | 8/2007 | Abdou |
| 2008/0208252 A1 | * | 8/2008 | Holmes ............... 606/232 |
| 2008/0275563 A1 | | 11/2008 | Makower |
| 2008/0288070 A1 | | 11/2008 | Lo |
| 2009/0036893 A1 | | 2/2009 | Kartalian et al. |
| 2009/0182336 A1 | | 7/2009 | Brenzel |
| 2009/0210010 A1 | * | 8/2009 | Strnad et al. ............... 606/280 |
| 2009/0287246 A1 | | 11/2009 | Cauldwell et al. |
| 2010/0076504 A1 | | 3/2010 | McNamara et al. |
| 2010/0082068 A1 | | 4/2010 | Graham |
| 2010/0152752 A1 | | 6/2010 | Denove et al. |
| 2010/0211071 A1 | | 8/2010 | Lettmann et al. |
| 2012/0016428 A1 | * | 1/2012 | White ............ A61B 17/0401 606/86 R |
| 2012/0130492 A1 | | 5/2012 | Eggli et al. |

FOREIGN PATENT DOCUMENTS

| | | |
|---|---|---|
| EP | 0998878 A1 | 5/2000 |
| EP | 0998878 | 9/2005 |
| WO | 2009/012001 A1 | 1/2009 |
| WO | WO 2009012001 | 1/2009 |
| WO | 2009/018527 A1 | 2/2009 |
| WO | WO 2009018527 | 5/2009 |
| WO | 2010/093696 A1 | 8/2010 |
| WO | WO 2010/093696 | 8/2010 |
| WO | WO 2010/106507 | 9/2010 |
| WO | WO 2012/029008 | 3/2012 |

OTHER PUBLICATIONS

"SportMesh Soft Tissue Reinforcement", Copyright 2006 Arthrotek Inc., http://faculty.washington.edu/alexbert/Shoulder/Surgery/ArthroscopicTechniques/Arthrotek/SportMeshSoftTissueReinforcemen%20.pdf, accessed Feb. 28, 2018, and herein after cited as Arthrotek.*
SportMesh Soft Tissue Reinforcement—Made from . . . Artelon Optimal Tissue Repair , Copyright 2007 Arthrotek Inc., https://www.yumpu.com/en/document/view/38380847/what-is-sportmesha-soft-tissue-reinforcement-biomet/7, accessed Apr. 20, 2018, and herein cited as Arthrotek 2.*
International application PCT/IB2011/053763 Search Report dated Jan. 30, 2012.
International Application # PCT/IB2011/053763 filed on Aug. 28, 2011.
International Application # PCT/IB2011/051155 Search Report dated Sep. 20, 2010.
Artimplant AB, "Artelon Tissue Reinforcement", year 2011 (http://www.artimplant.com/patients/artelon-tissue-reinforcement.html).
Depuy Mitek, Inc., "Fastin® RC Dual-Channeled Anchor", year 2007.
Artimplant—Artelon Tissue Reinforcement; <http://www.artimplant.com/patients/artelon-tissue-reinforcement.html> (2011).
DePuy Mitek by Johnson and Johnson; Fastin RC Dual-Channeled Anchor (2007).
Arnold et al."Biomechanical In Vitro-Stability Testing on Human Specimens of a Locking Plate System Against Conventional Screw Fixation of a Proximal First Metatarsal lateral Displacement Osteotomy", The open Orthopedics Journal, 2012, 6, 133-139.
International Search Report for PCT/IL2013/050362 dated Sep. 13, 2013.

* cited by examiner

HALLUX ABDUCTO VALGUS ASSEMBLIES

CROSS-REFERENCE TO RELATED APPLICATION

This application claims the benefit of U.S. Provisional Patent Application 61/160,736, filed Mar. 17, 2009.

FIELD AND BACKGROUND OF THE INVENTION

The present invention generally relates to orthopedic surgery and, more particularly but not exclusively, to surgical assemblies and methods for correcting hallux abducto valgus.

Hallux abducto valgus (HAV) is a deformity primarily of the forefoot involving lateral deviation of the great toe, and medial deviation of the first metatarsal.

In an HAV deformity, a point is reached in which the muscles migrate laterally beyond the $1^{st}$ metatarsal phalangeal joint lateral boundary. Once this stage has been reached, the deformity is self-feeding, as the muscles gain inordinate mechanical advantage, causing further angular deviation so that the hallux abducto valgus deformity becomes progressively more pronounced.

The severity of HAV deformities has traditionally been quantified through measurements of X-ray radiographs. The first of the two most common measurement or quantification techniques for hallux abducto valgus deformity is the $1^{st}$ intermetatarsal (IM) angle. The $1^{st}$ IM angle is the angle defined by the intersection of lines made along the longitudinal axes of the first and second metatarsal shafts. This angle is normally about six degrees; the upper normal limit is about nine degrees.

The second measurement that defines an HAV deformity is the 1st Metatarsal Phalangeal Joint (MPJ) angle, which is defined by the intersection of lines made along the longitudinal axes of the first metatarsal shaft and the proximal phalanx of the hallux, alternatively referred to as the first toe, or great, toe.

A normal maximum for a $1^{st}$ MPJ angle is between nine and ten degrees. An MPJ angle measurement of 12 degrees would be almost uniformly regarded as abnormal.

An HAV deformity typically includes both an abnormally high $1^{st}$ IM and an abnormally high $1^{st}$ MPJ angle; with a severe HAV deformity including a $1^{st}$ IM angle of 15 degrees or more; and a $1^{st}$ MPJ angle of 35 degrees or more.

A severe HAV deformity, in addition to being unsightly, is painful in most footwear, even footwear having extra wide widths. Sufferers of severe HAV deformities generally are limited to wearing non-aesthetic shoes that have a special out-pocketing in the forefoot to accommodate the displaced bones.

In some instances of HAV, for example in moderate HAV bone deviation, surgical correction is an aesthetic consideration. In other instances of HAV, surgical correction, particularly in severe HAV bone deviation, is a medical imperative, for example to prevent ulceration, infection, and/or amputation.

Surgical correction of HAV deformity often requires osseous correction, for example an osteotomy comprising a bone wedge of the proximal and/or distal first metatarsal; and an osteotomy comprising a bone wedge of the first proximal phalanx. In addition, surgical correction usually requires remodeling of a bunion deformity, comprising, inter alia, a medial out pocketing of bone over the $1^{st}$ MPJ.

Osseous correction may not produce satisfactory long-term results due to continued abnormal forces exerted by the muscles and ligaments, which often cannot be fully realigned during surgery; and/or continued biomechanical imbalance in the foot during gait.

The abnormal forces pull the bones of the $1^{st}$ MPJ and $1^{st}$ metatarsal toward the original abnormal angles. Malunion and non-union have also been recorded in cases of HAV osseous correction.

Relevant Prior Art includes U.S. Pat. No. 4,159,716 (Borchers).

SUMMARY OF THE INVENTION

According to an aspect of some embodiments of the invention, there is provided an assembly for in vivo alignment of two or more bones in a living body. The assembly comprises a cannulated sleeve configured to secure in a bore in a first bone, a mesh body having a proximal arm configured to be engaged by the cannulated sleeve, and a distal arm configured to be secured to a portion of a second bone. The assembly further includes a fastener configured to secure the distal arm to the portion of the second bone.

According to another aspect of some embodiments of the invention, there is provided a method for reducing an interphalangeal joint angle, the method comprising the steps of: entering the tissues of the foot affected with hallux valgus by performing at least one incision, shaving an exostosis, and reducing the first metatarsal phalangeal joint.

In some embodiments of the invention, the assembly further comprises an elongate flexible member configured to pass through a cannulation of the cannulated sleeve.

In some embodiments of the invention, the elongate flexible member includes a first end including a first securing device configured to the cannulated sleeve.

In some embodiments of the invention, the elongate flexible member includes a second end including a second securing device configured to secure to the cannulated sleeve.

According to still another aspect of some embodiments of the invention, there is provided a method for reducing an intermetatarsal angle, the method comprising the steps of: drilling a bore through a first metatarsal, drilling a bore through a second metatarsal, and reducing the angle between the first metatarsal and the second metatarsal.

In some embodiments of the invention the first securing device comprises at least one of: a tack, a screw, and a clamp.

In some embodiments of the invention the second securing device comprises at least one of: a tack, a screw, at least one wing, and at least one pivotable member.

In some embodiments of the invention at least one of: the cannulated sleeve, the mesh body, the elongate flexible member, the first securing device, and the second securing device, include at least one of: a biodegradable material, a soft-tissue infiltration-promoting material, an osteogenic compound; and a bone-growth promoting compound.

According to a further aspect of some embodiments of the invention, there is provided an assembly for use in the correction of hallux abducto valgus, the assembly comprising: a first connector configured to be affixed to a first bone, a second connector configured to be affixed to a second bone, and an elongate member having been configured to span between the first bone and the second bone, the elongate member having: a first portion configured to be affixed to the first bone by the first connector, and a second portion configured to be affixed to the second bone by the second connector.

In some embodiments of the invention, the assembly includes a flexible material including a first portion configured to be affixed to the first bone by the connector.

In some embodiments of the invention, the flexible material includes a second portion configured to be affixed to a third bone by a third connector.

According to additional aspect of some embodiments of the invention, there is provided an anchor system for use in the repair of hallux abducto valgus, the system comprising: a primary anchor adapted to engage a first bone, a secondary anchor adapted to engage a second bone, an elongate bone spanning connector extending between the primary and secondary anchors, a joint spanning material having: a first portion affixed to the primary anchor engaging the first bone, and a second portion configured to span a joint and connect to a third bone, and a tertiary connector configured to connect the second portion of the joint-spanning material to the third bone.

In some embodiments of the invention, the primary anchor comprises a hollow portion, and the elongate bone-spanning connector is of a diameter that is configured to pass through the hollow portion.

In some embodiments of the invention, the primary anchor is configured to be affixed to the first bone by at least one of: screw threads, and a ledge.

In some embodiments of the invention, the secondary anchor is configured to assume at least one configuration wherein the secondary anchor is configured to pass through the hollow portion.

In some embodiments of the invention the secondary anchor is configured to assume at least one configuration wherein the secondary anchor is configured to pass through a bore through at least a portion of at least one of: the first bone, and the second bone.

According to still another aspect of some embodiments of the invention, there is provided a method for reducing a hallux abducto valgus deformity, the method comprising: drilling a bore through a first metatarsal and through a second metatarsal, passing a fixation member attached to a first end of one elongate flexible member through the bore, affixing the fixation member to juxtapose against the second metatarsal, tensioning the elongate flexible member to reduce an intermetatarsal angle between the first metatarsal and the second metatarsal, and securing a second end of the fixation member to the first metatarsal.

In some embodiments of the invention, the fixation member comprises at least one rotatable member configured to be rotated by the elongate flexible member.

In some embodiments of the invention, the method includes affixing the second end of a securing member to the first metatarsal.

In some embodiments of the invention, the method includes securing a first portion of an elongate material to a medial portion of the first metatarsal.

In some embodiments of the invention, the method includes securing a second portion of the elongate material to a medial portion of a first proximal phalanx.

In some embodiments of the invention, the method includes applying tension to the elongate material to cause reduction in the first metatarsal phalangeal joint.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods, and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings.

DESCRIPTION OF EMBODIMENTS OF THE INVENTION

Figure 1:
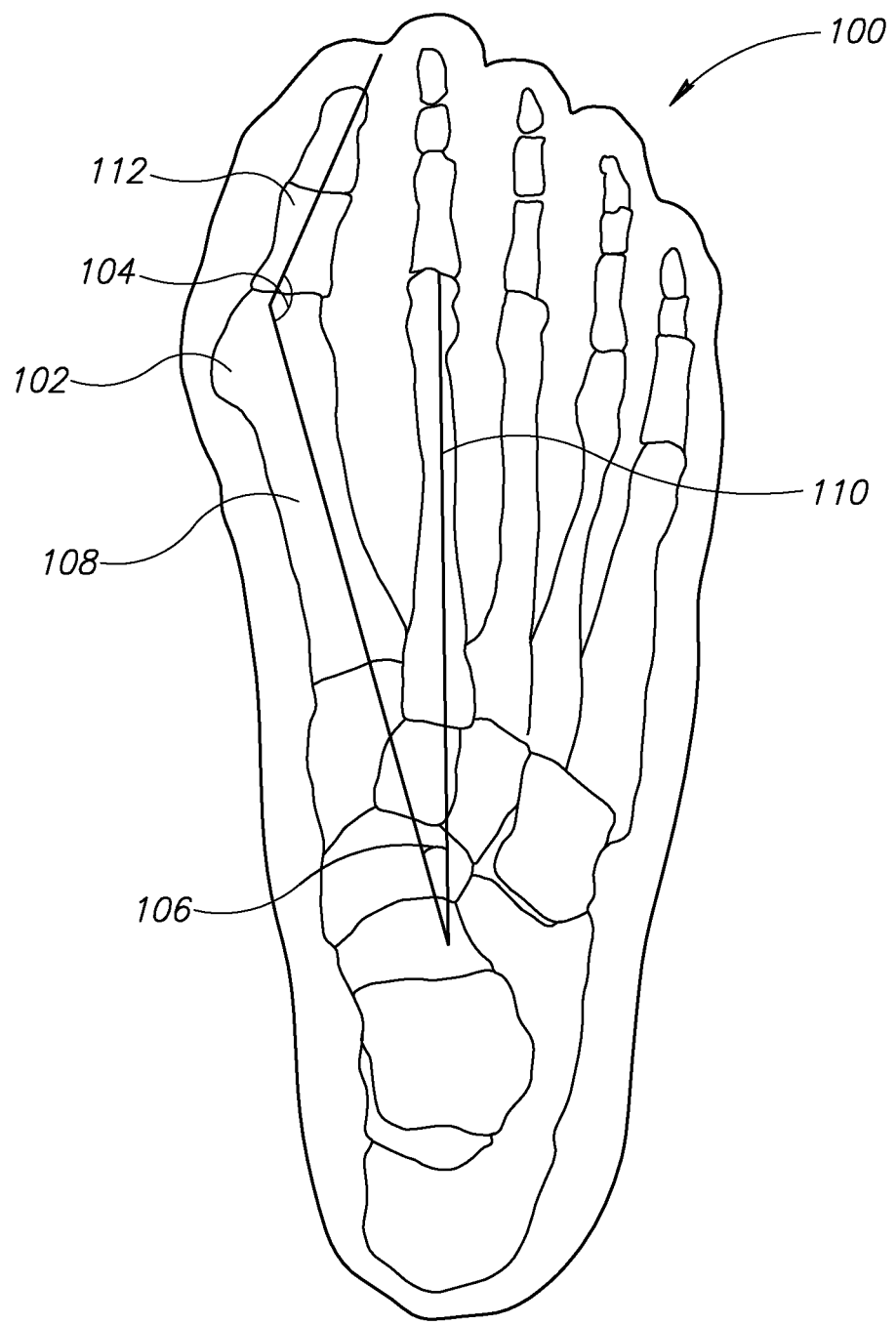
FIG. 1 shows a typical hallux abducto valgus deformity.
Figure 2:
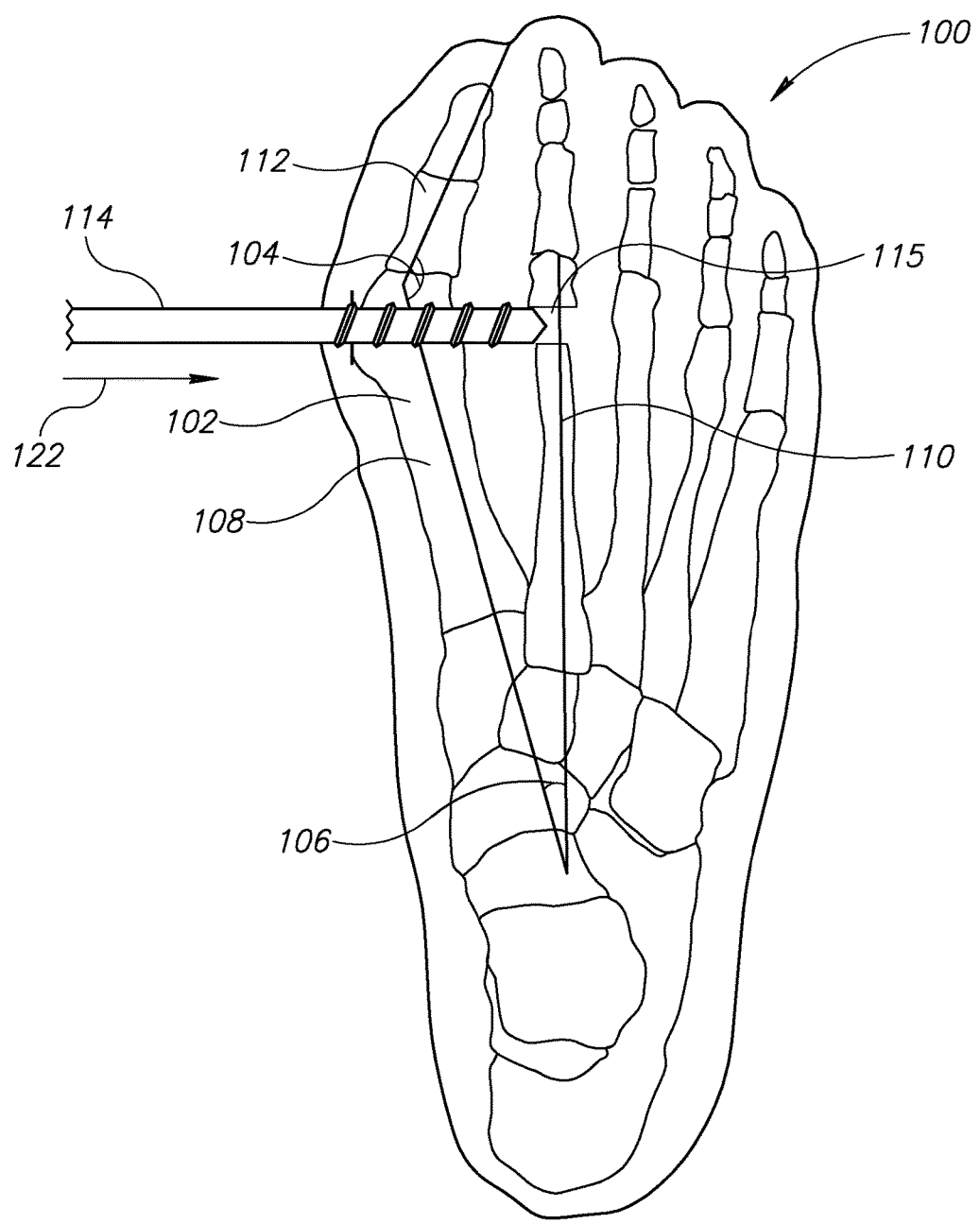
FIGS. 2-8 show reduction of and intermetatarsal angle, according to some embodiments of the invention.

The present invention generally relates to orthopedic surgery and, more particularly but not exclusively, to surgical assemblies and methods for correcting hallux abducto valgus.

Before explaining at least one embodiment of the invention in detail, it is to be understood that the invention is not necessarily limited in its application to the details of construction and the arrangement of the components and/or methods set forth in the following description and/or illustrated in the drawings. The invention is capable of other embodiments or of being practiced or carried out in various ways.

Referring to the drawings:

For purposes of better understanding some embodiments of the present invention, reference is first made to the anatomy of a conventional Hallux Abducto-Valgus (HAV) deformity.

As shown in FIG. 1, a foot 100 having an HAV deformity includes an abductus position, of a first metatarsal 108, meaning that first metatarsal 108 is splayed medially, toward the middle line of the body.

As noted above, the magnitude of the abductus is measured by the angle between first metatarsal 108 and a second metatarsal 110 and referred to as a first intermetatarsal angle 106.

Additionally, an HAV deformity includes a significant deviation between first metatarsal 108 and a proximal first phalanx 112 is known as a 1st Metatarsal Phalangeal Joint (MPJ) angle 104.

In addition, an HAV deformity typically includes a severe medial out-pocketing of bone at the distal portion of first metatarsal 102, referred to as a medial exostosis 102, or a bunion 102.

While the present invention is described with respect to HAV reconstruction, there are a variety of surgical applications that the present invention can address with minor modification to the embodiments described. For example, embodiments of the present invention may be utilized in correcting phalangeal deviation of fingers, for example:

i) in traction to prevent progressive "trigger finger" or phalangeal deformities for example associated with Dupuytren's contracture; and ii) in treating Boutonniere deformity caused by an injury to phalangeal tendons;

Alternatively, the present invention may be used in the lesser phalanges of the foot, for example in realignment of a hammer toe or mallet toe.

The many applications of embodiments of the present invention are well known to those familiar with the art.

$1^{st}$ MPJ Joint Reconstruction

In many surgical corrections of HAV, prior to removal of bunion deformity 102, minimal incision surgical technique is employed, for example using a balloon that is inserted through a small medial incision and inflated over bunion deformity 102 thereby separating soft tissue from bunion 102, portions of phalanx 112 and/or portions of first metatarsal 108.

Additionally, the balloon is typically used to move the nerves of first metatarsal 108 and proximal first phalanx 112 away from proximity to the bones, thereby protecting the nerves during subsequent reconstruction of HAV of foot 100.

In further embodiments, the balloon can be used in the region of the subtalar joint, to can help reduce intra articular fractures of the calcaneus, and fractures of the foot and ankle.

Bunion deformity 102 is then surgically excised utilizing mini instrumentation that is inserted through the above noted, or additional, small incisions in order to remove portions of deformity 102 from foot 100; and/or to create one or more of the above-noted osteotomies.

Optionally the present invention contemplates utilizing minimal incision surgical technique, meaning a small incision through the soft tissue proximate to bunion deformity 102.

A minimal incision technique promotes rapid post-operative healing of a surgical correction of an HAV deformity of foot 100. Additionally, due to the short length of the incision (s), there is typically less scar formation so that movement between first metatarsal 108 and first phalanx 112 is greater, and/or less painful than in surgery through larger incisions, often referred to as "open" surgery.

However, it should be noted that the present invention may be utilized in surgical techniques that do not utilize minimal incision technique, should the necessity arise. Open surgical technique, may be required, for example, when extensive remodeling of foot 100 is required in more than the transverse plane defined by 1st Metatarsal Phalangeal Joint angle 104 and first intermetatarsal angle 106.

The many surgical methods and techniques that can be used in conjunction with the present invention are well known to those who are familiar with the art.

The present invention contemplates a variety of assemblies that include multiple devices, and associated methods of deployment, for the correction of first intermetatarsal angle 106 and/or 1st Metatarsal Phalangeal Joint angle 104. The assemblies, assembly components and methods which are initially described herein, are just some of many assemblies, assembly components and methods that may be contemplated.

No matter whether an open surgery or minimal incision surgery is performed, a majority of bunion deformity 102 is usually removed until the area of bunion deformity 102 is flush, or almost flush, with the medial cortex of first metatarsal 108.

Joint Remodeling

In the presence of significant cartilaginous erosion, quite common in the presence of a high IM angle 106 and/or a high MPJ angle 104, cartilaginous remodeling may be required. Such remodeling may be prior to, or concurrent with, reduction of high MPJ angle 104, as described below.

In some embodiments of the invention, a cartilaginous pad is grown in advance of the HAV surgery in which the initiator cells of the cartilaginous pad are pre-harvested from the recipient and grown in a laboratory to form the cartilaginous pad.

If implantation of the cartilaginous pad is performed, in addition to removing bunion deformity 102, existing cartilage on the head of $1^{st}$ metatarsal 108 and/or base of $1^{st}$ proximal phalange 112 are shaved in preparation for receiving and fusing with the cartilaginous pad.

The shaver used in the procedure may be introduced through the existing minimal incision or through a second minimal incision, for example a dorsal incision proximate to the joint space between the head of $1^{st}$ metatarsal 108 and base of $1^{st}$ proximal phalange 112.

Following cartilaginous shaving and/or remodeling, the above-noted cartilage pad is secured on the head of $1^{st}$ metatarsal 108 and/or base of 1st proximal phalange 112; and such cartilaginous pads and associated surgical installation technique are contemplated in conjunction with the present invention.

Correction of $1^{st}$ IM Angle

Figure 3:
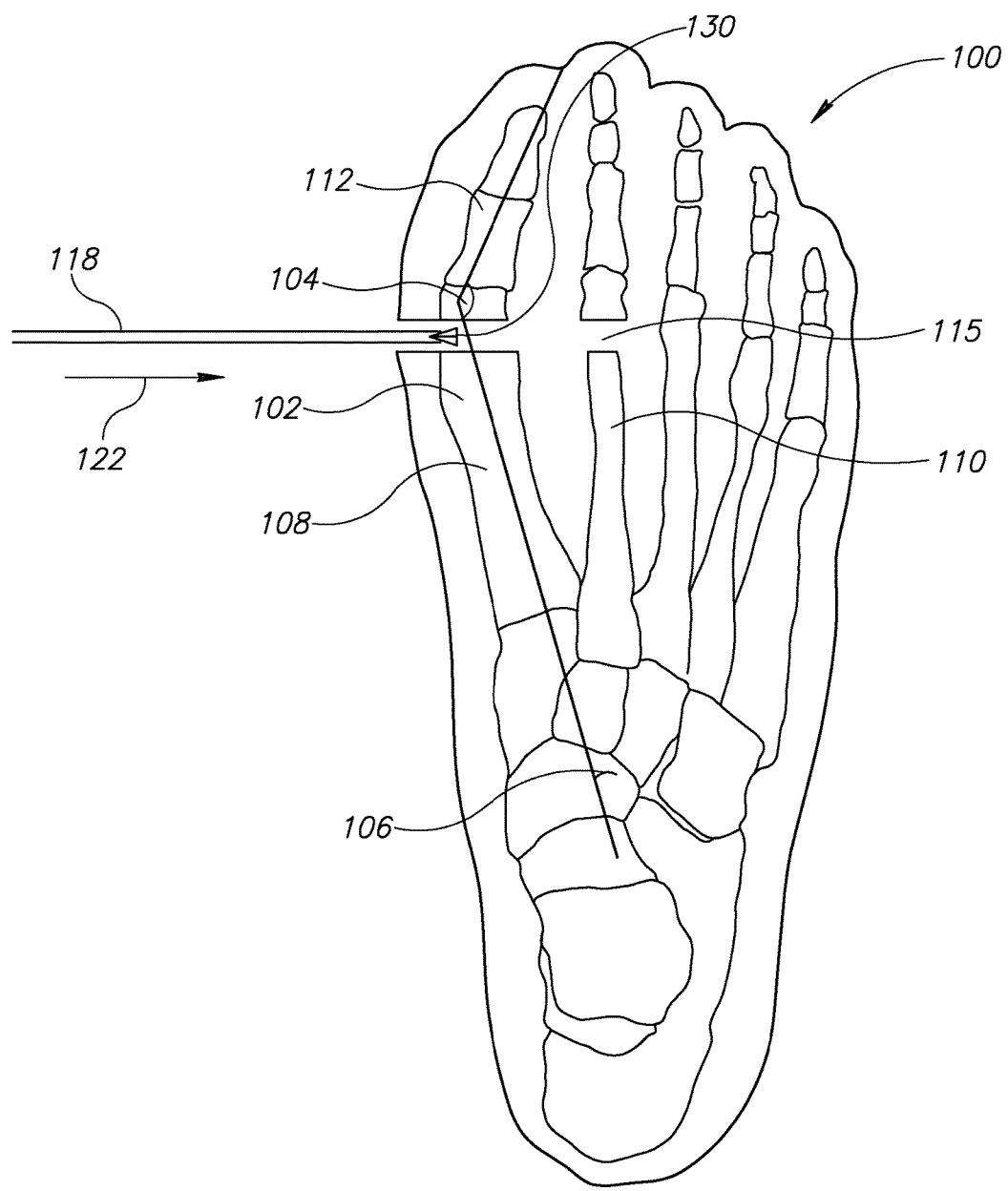
Figure 5:
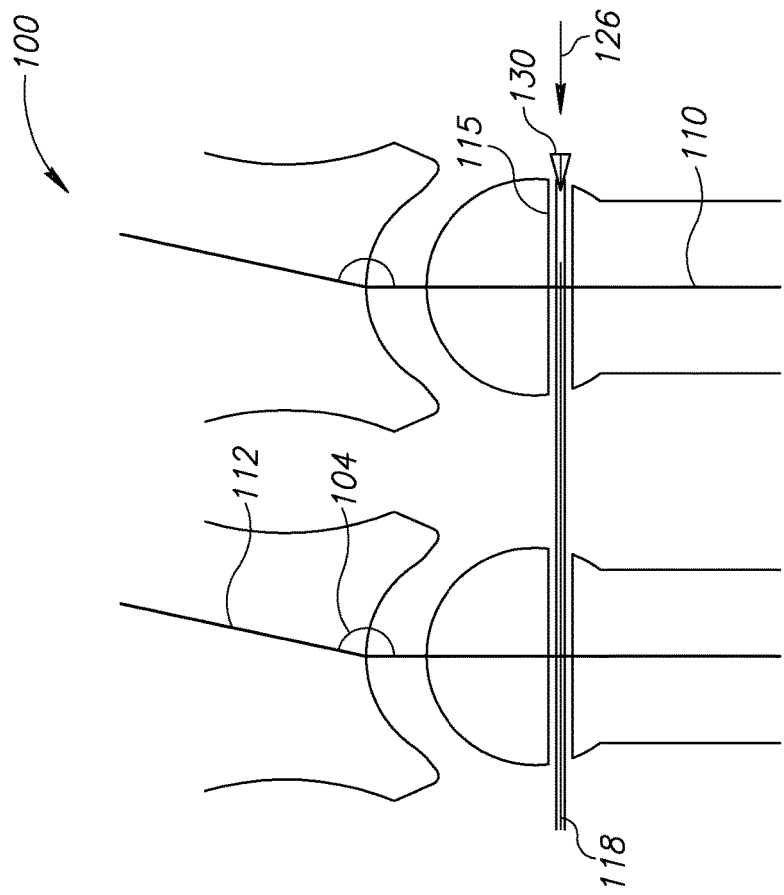
Figure 4:
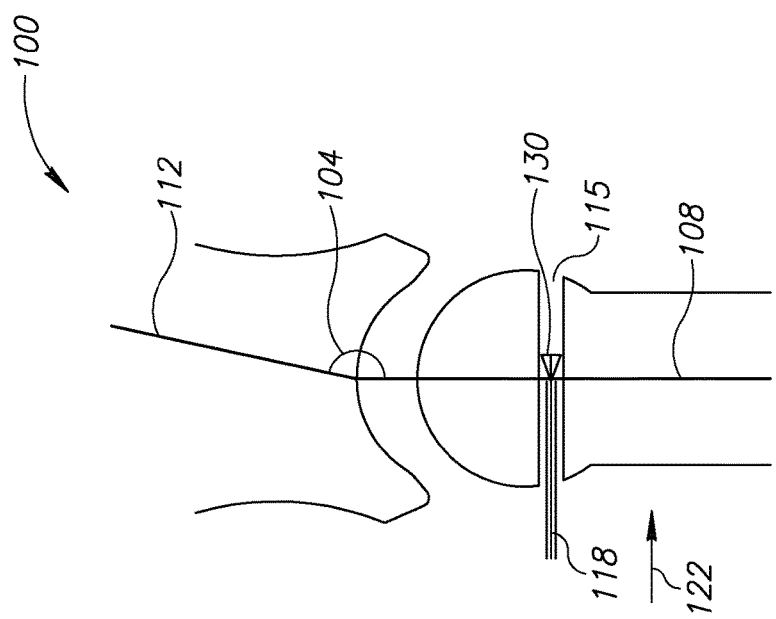
Figure 6:
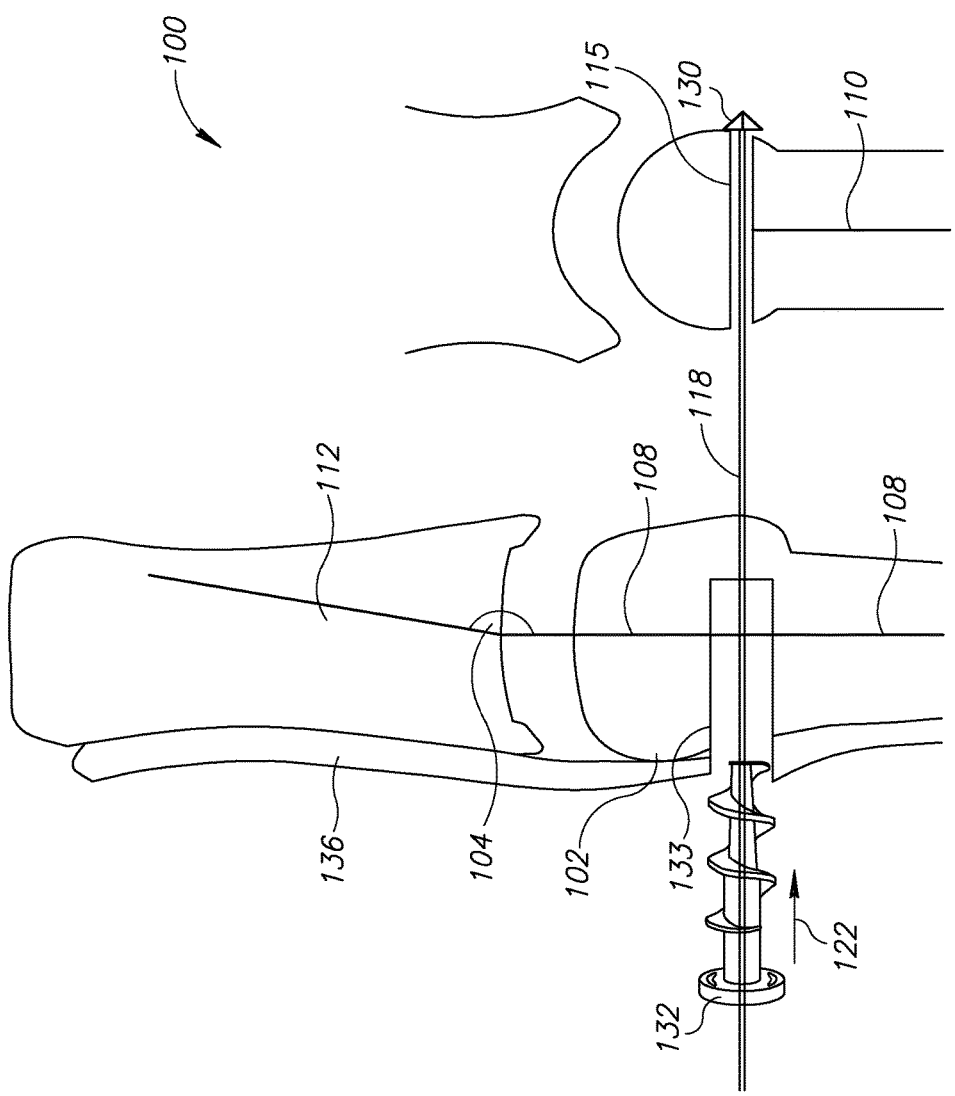

Referring to FIGS. 3 and 4, a flexible rod 118 having a wing end 130 is passed through bore 115 in direction 122, until, as seen in FIG. 5, wing end 130 passes completely through second metatarsal 110. Flexible rod 118 is then manipulated and pulled in a direction 126, which is a medial direction 126, until wing end 130 spreads out across the lateral cortex of second metatarsal 110, as seen in FIG. 6.

At this time a fibrous membrane 136 is placed along first metatarsal 108 and first phalanx 112; a placement that may be accomplished utilizing the above-noted minimal incision surgical technique.

A bore 133 is made through fibrous membrane 136 and partially through first metatarsal 108. A longitudinally hollow screw 132 is introduced into bore 133 and passed so that the bore of longitudinally hollow screw 132 slides along flexible rod 118 in direction 122.

Figure 7:
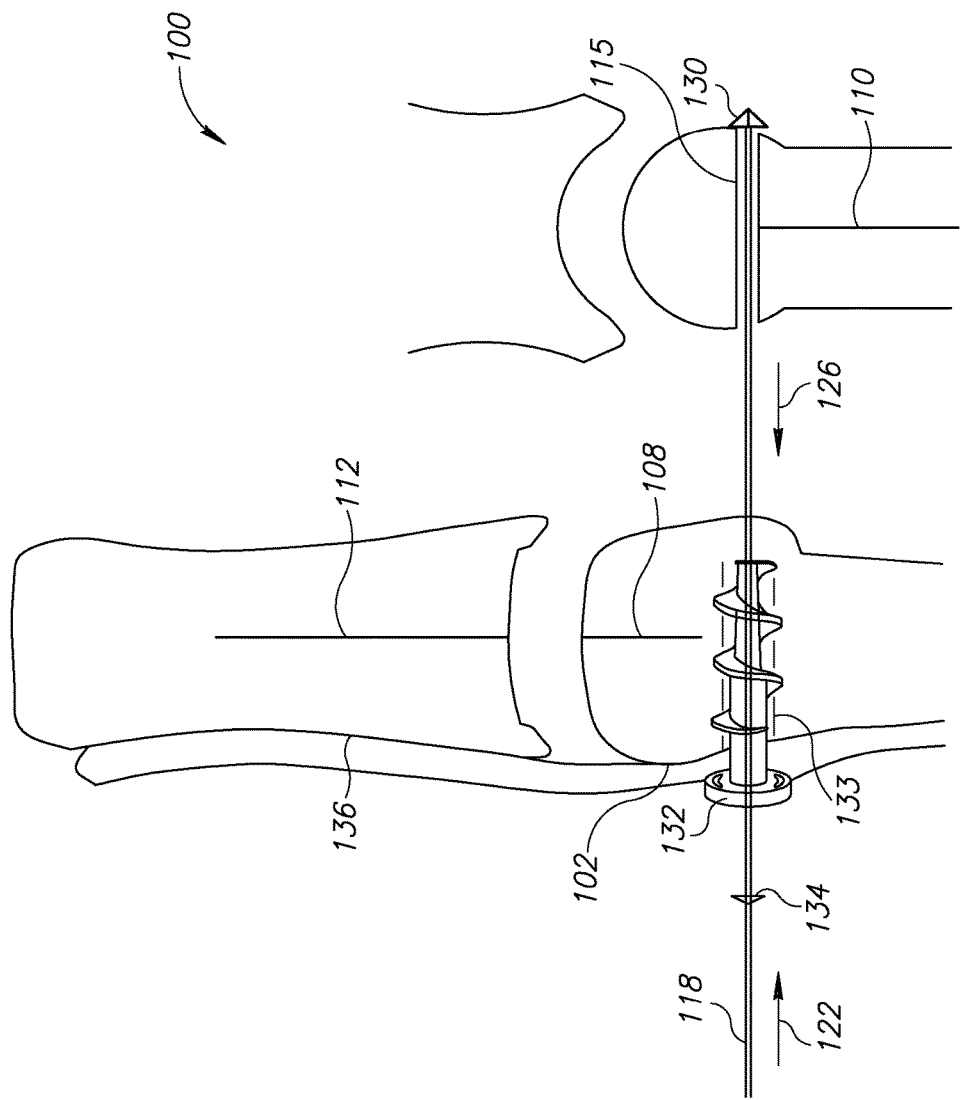
Figure 8:
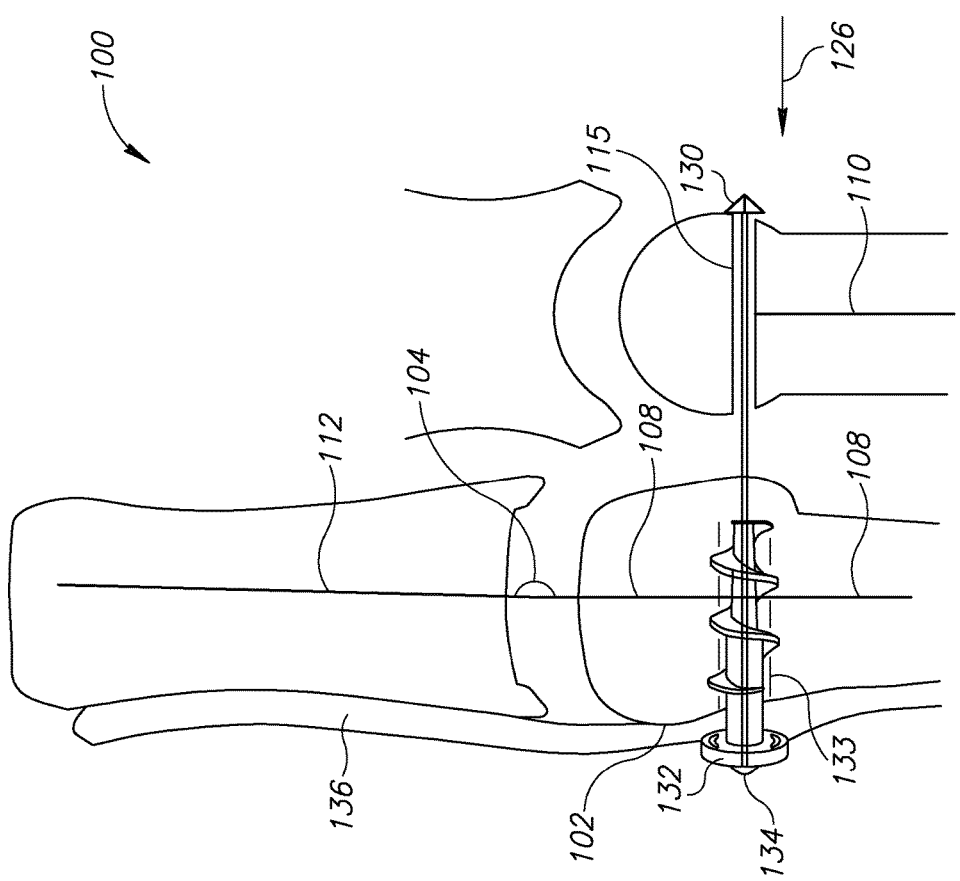

As seen in FIG. 7 longitudinally hollow screw 132 is in place and flexible rod 118 is pulled in direction 126 until reduction of the distance between first metatarsal 108 and second metatarsal 110 is attained. A clamp 134 is moved along flexible rod 118 until, as seen in FIG. 8, clamp 134 is flush against the head of hollow screw 132. Clamp 134 is then clamped for example using a surgical plier, thereby maintaining the correction between first metatarsal 108 and second metatarsal 110.

As seen in FIG. 8, flexible rod 118 has been cut flush with clamp 134.

Correction of $1^{st}$ MPJ Angle

Figure 9:
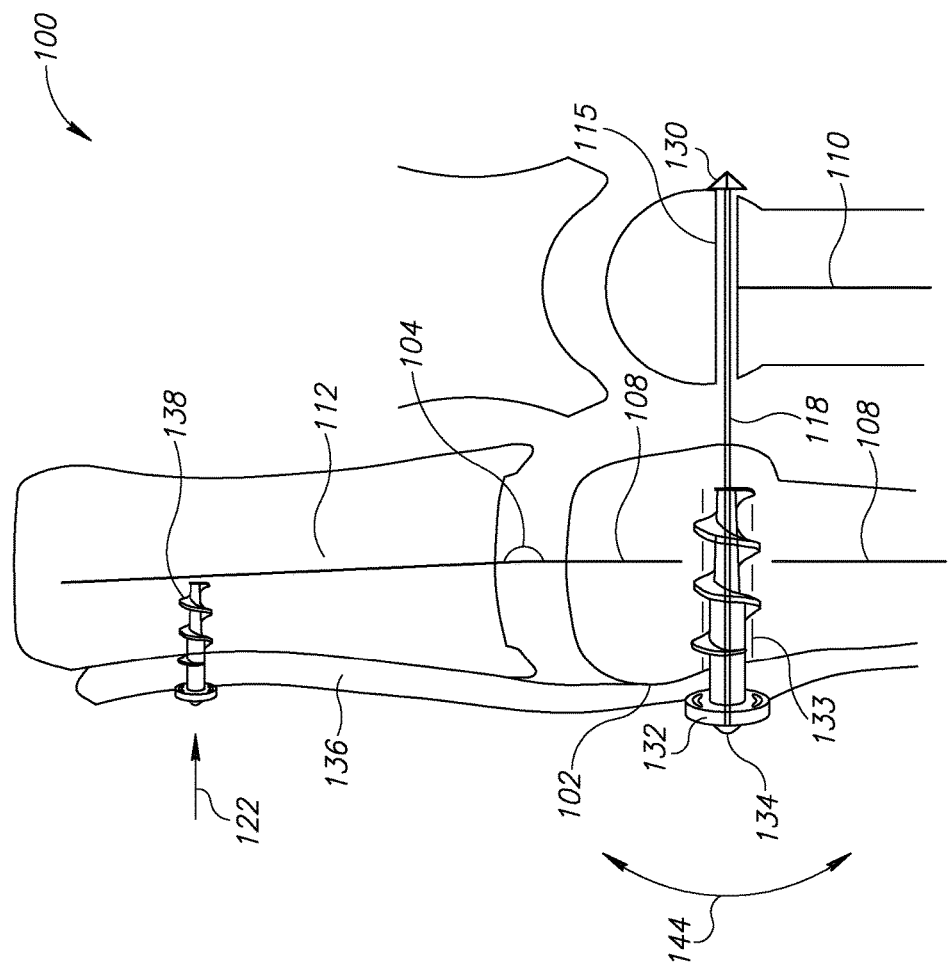
FIGS. 9-10 show reduction of the hallux abducto valgus using a corrective assembly, according to some embodiments of the invention.

Referring to FIG. 9, attention of the surgeon is directed to 1st Metatarsal Phalangeal Joint angle 104 and the distal end of first phalanx 112 is moved in direction 122 until properly aligned on first metatarsal 108 such that 1st Metatarsal Phalangeal Joint angle 104 has been reduced to an acceptable magnitude.

The cartilaginous pad and surgical installation procedure noted above may be utilized prior to reduction of 1st Metatarsal Phalangeal Joint angle 104.

A phalangeal screw 138 is introduced through fibrous membrane 136 and into first phalanx 112 to stretch fibrous membrane 136 so that stretched fibrous membrane 136 maintains the correction between proximal phalanx 112 and first metatarsal 108.

Hallux Abducto Valgus Correction

Figure 10:
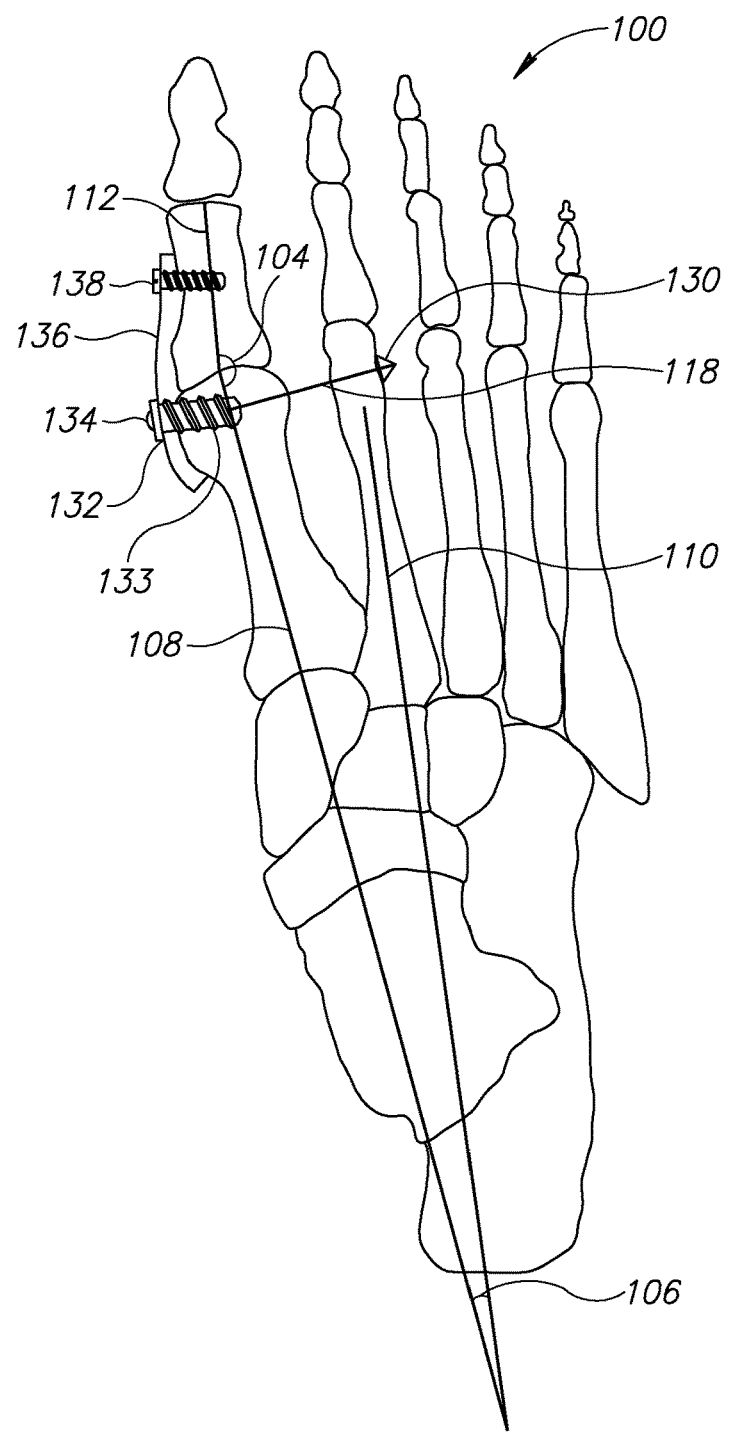

FIG. 10 shows foot 100 wherein intermetatarsal angle 106 has been reduced by the tension of flexible rod 118 in a substantial manner so that splay between first metatarsal 108 and second metatarsal 110 is within normal limits.

Additionally, fibrous membrane 136 spanning the joint between first proximal phalanx 112 and first metatarsal 108 has reduced the 1st MPJ angle 104 to within normal limits.

Based upon the many materials that could be utilized in the current invention, the hallux abducto valgus correction will optionally become intrinsic to foot 100, meaning that the assembly used in correction of foot 100 will become at least partially replaced with biomechanically functional tissue.

The following description presents but a few of the many materials that encourage tissue ingrowth and/or tissue replacement, either in part or fully, by natural tissues of the body.

Materials

Flexible rod 118, for example, optionally comprises materials that encourage ingrowth of tissue that recreate and maintain the anatomic position and mechanical properties of an original adductor ligament that spans between first metatarsal 108 and second metatarsal 110.

Additionally, fibrous membrane 136 is contemplated to be made of fibrous materials that similarly encourages ingrowth of soft tissue to reform the medial capsule surrounding the joint between first metatarsal 108 and first phalanx 112, and additionally provides mechanical advantage to maintain the alignment of 1st Metatarsal Phalangeal Joint angle 104 by virtue of the attachments to phalanx 112 and first metatarsal 108.

Just one example of the many presently existing soft tissue materials that encourage ingrowth and/or duplication of biological soft tissue structure is the Artelon® Tissue Reinforcement, manufactured by Artimplant AB of Vastra Frolunda, Sweden.

Furthermore, fasteners comprising for example screws 132 and 138, clamp 134, and/or winged end 130 are optionally composed of biocompatible materials that after a period of, for example, between one and four years; encourage bony ingrowth and/or dissolve, such that the bones of foot 100 optionally revert to a natural biological state.

Just one example of the many presently existing fasteners that dissolve, encourage bony ingrowth, and/or encourage replacement of biological structures are those that include materials such as Polylactic acid, which is a polymer of lactic acid.

The many materials that dissolve, encourage bony ingrowth, and/or encourage replacement of biological structures are well known to those familiar with the art. Additionally, as noted below, the scope of the instant invention is intended to include all new materials and material technologies that are developed in the future, a priori.

Alternate Embodiments

As noted above there are a variety of assemblies, assembly components and methods that can be utilized in the present invention and just one of the many alternative assemblies, assembly components and methods is now presented.

Figure 11:
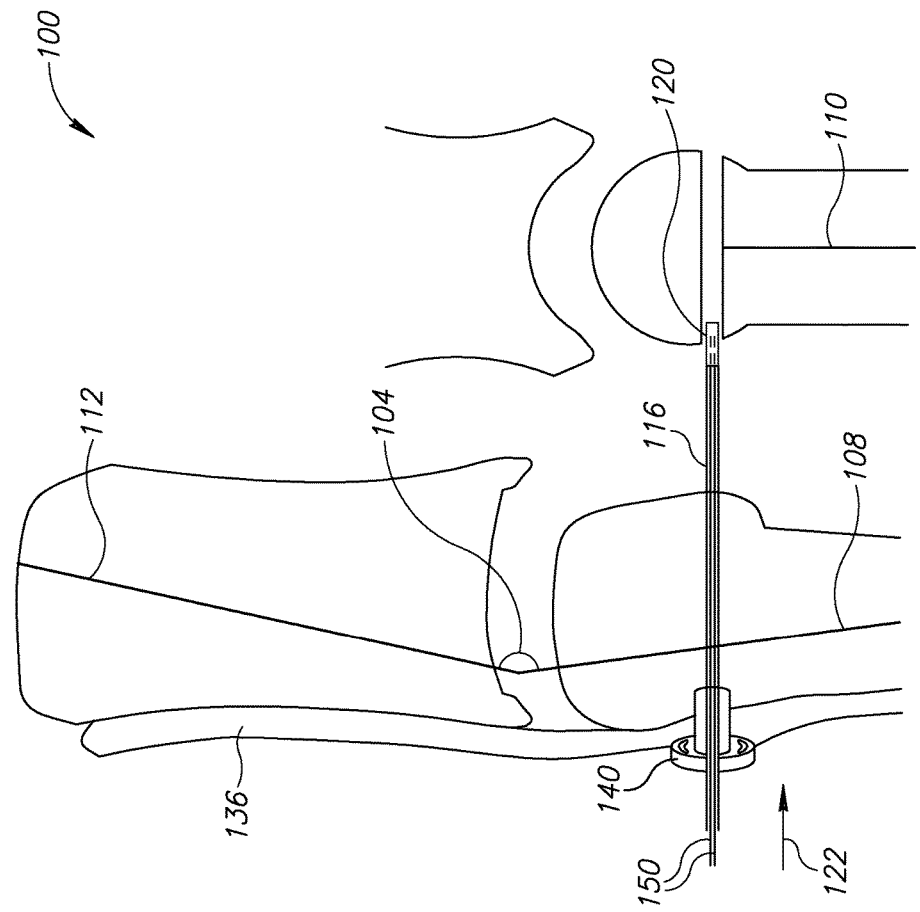
FIGS. 11-13 show an alternative embodiment of the corrective assembly shown in FIGS. 9-10, according to some embodiments of the invention.

Referring to FIG. 11, a hollow tack 140 is pressed through fibrous membrane 136 and a hollow tube 116 is pressed in direction 122 through the longitudinal bore of hollow tack 140.

Figure 12:
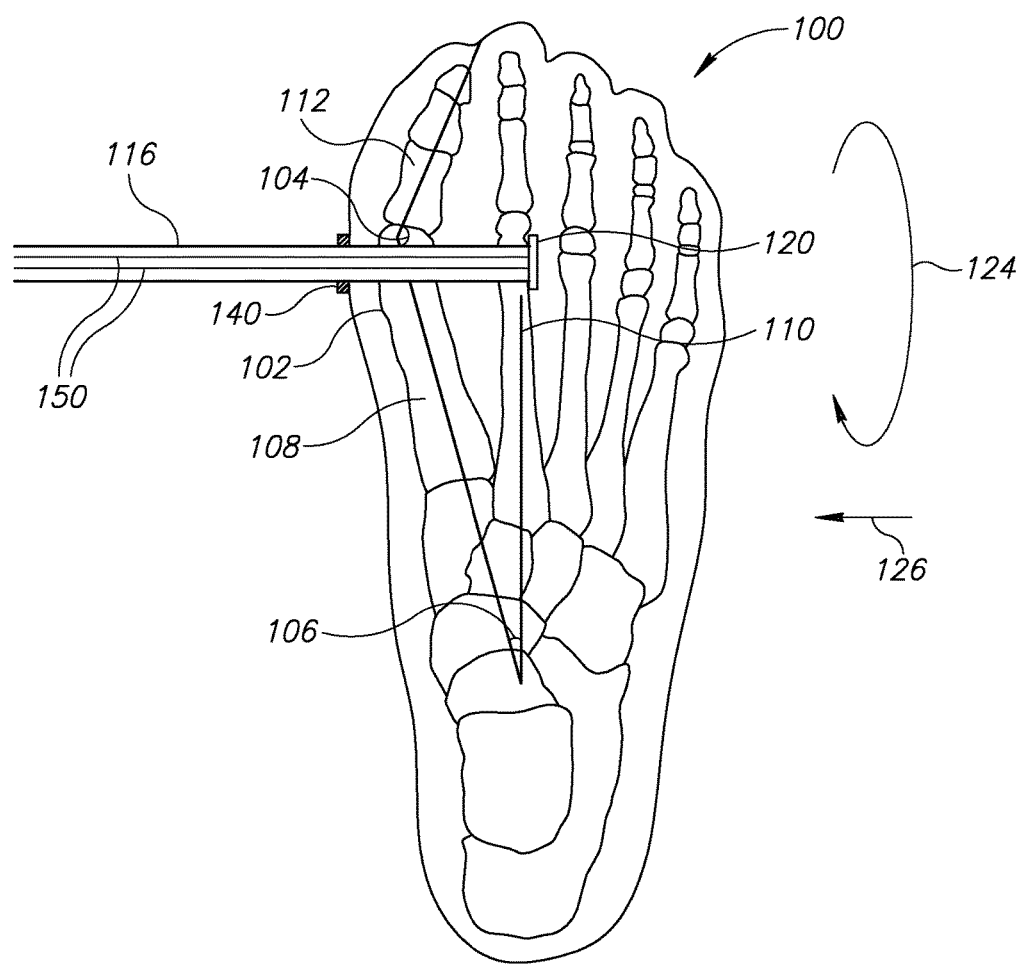

Hollow tube 116 contains dual fibers 150 that are attached to an elongate button 120 at the end of tube 116. As seen in FIG. 12 dual fibers 150 are manipulated to rotate elongate button 120 in a direction 124 so that the longitudinal axis of elongate button 120 becomes substantially parallel to the head of second metatarsal 110.

Dual fibers 150 are then pulled in direction 122 and secured against hollow tack 140 to maintain the correction; for example by tying a traditional suture knot.

Figure 13:
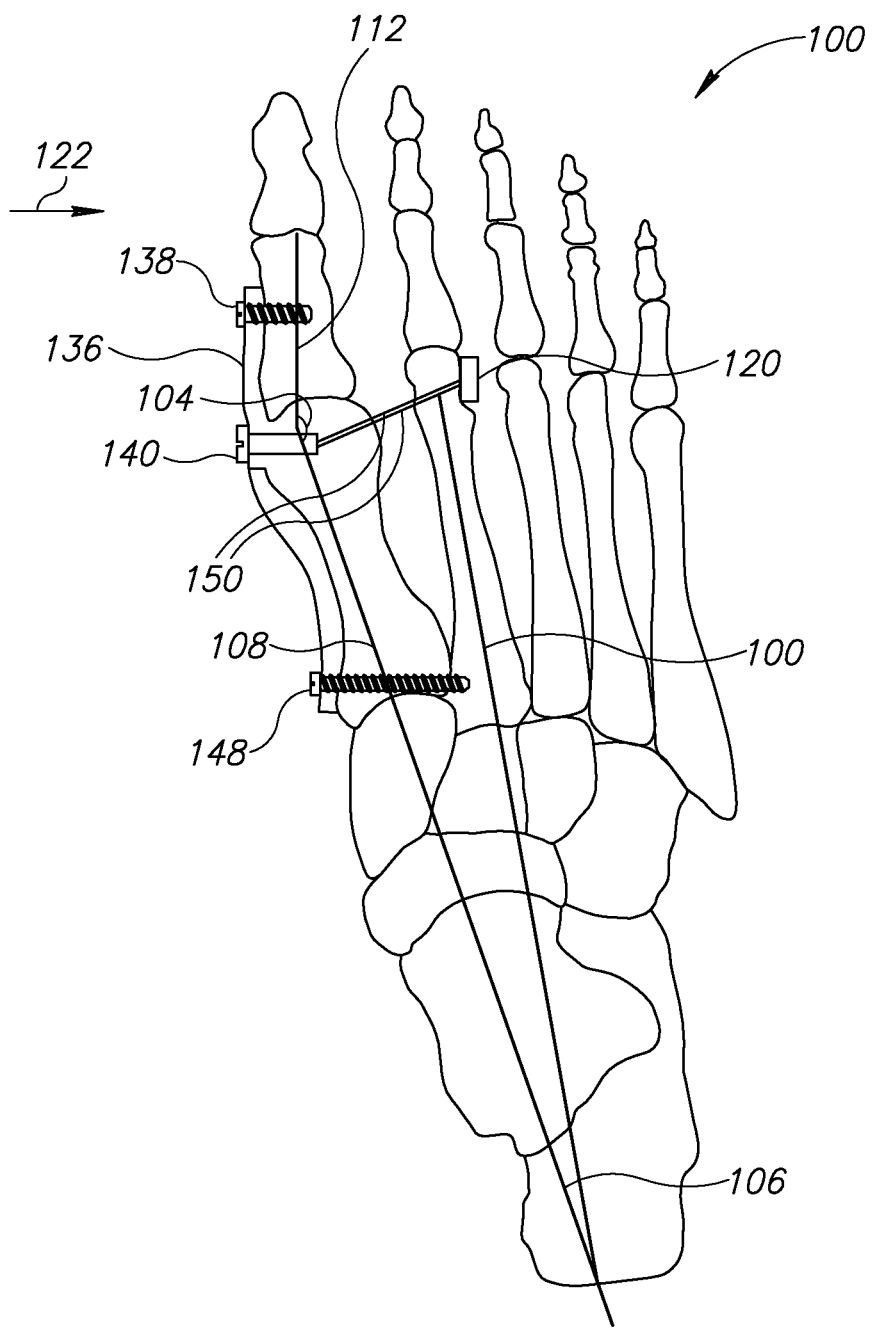

Alternatively clamp 134 (FIG. 8) or an analogous device that clamps or crimps dual fibers 150, is used to secure dual fibers 150 against hollow tack 140. Additionally, as seen in FIG. 13, fibrous membrane 136 is secured with screw 138 to proximal phalanx 112.

In some embodiments, screw 138 is replaced with an alternative device, for example a "Mitek anchor" manufactured by DePuy Mitek, Inc., Raynham, Mass. The many options for securing fibrous mesh 136 to proximal phalanx 112 may include any securing devices already known or to be developed in the future; and the many possible securing configurations presently existing, are well-known to those familiar with the art.

In some embodiments of the invention, fibrous mesh membrane 136 optionally extends along first metatarsal 108 at least to mid shaft or even to the base of first metatarsal 108 and is secured to first metatarsal 108 with a metatarsal screw 148.

In some deformities of foot 100, it may be desirable to fuse and/or stabilize the base of first metatarsal 108 and second metatarsal 110. To accomplish such fusion and/or stabilization, as shown, metatarsal screw 148 is of sufficient length to secure in second metatarsal 110.

The many options for embodiments of the present invention and surgical techniques that allow for reconstruction of foot 100, for example in multiple planes as noted above, are well known to those that are familiar with the art.

It is expected that during the life of a patent maturing from this application many relevant Hallux Abducto Valgus correction materials and/or assemblies will be developed and the scope of the phrase "Hallux Abducto Valgus correction materials and/or assemblies" is intended to include all such new technologies a priori.

As used herein the term "about" refers to ±10%.

The terms "comprises", "comprising", "includes", "including", "having", and their conjugates mean "including but not limited to". This term encompasses the terms "consisting of" and "consisting essentially of".

The phrase "consisting essentially of" means that the composition or method may include additional ingredients and/or steps, but only if the additional ingredients and/or steps do not materially alter the basic and novel characteristics of the claimed composition or method.

As used herein, the singular form "a", "an", and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity, and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques, and procedures for accomplishing a given task including, but not limited to, those manners, means, techniques, and procedures either known to, or readily developed from known manners, means, techniques, and procedures by practitioners of the chemical, pharmacological, biological, biochemical, and medical arts.

As used herein, the term "treating" includes abrogating, substantially inhibiting, slowing or reversing the progression of a condition, substantially ameliorating clinical or aesthetical symptoms of a condition, or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination, or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications, and variations will be apparent to those skilled in the art. Accordingly, it is intended to embrace all such alternatives, modifications, and variations that fall within the spirit and broad scope of the appended claims.

All publications, patents, and patent applications mentioned in this specification are herein incorporated in their entirety by reference into the specification, to the same extent as if each individual publication, patent, or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. Surgical apparatus, comprising:
a stretchable elastic fibrous membrane, comprising proximal and distal arms;
a first fastener, which is configured to secure the proximal arm of the fibrous membrane to a first bone;
a second fastener, which is configured to secure the distal arm of the fibrous membrane to a second bone so as to align the second bone relative to the first bone;
a third fastener, which is configured to engage a third bone, adjacent to the first bone; and
an elongate flexible member, which is configured to be fastened between the first and third fasteners so as to reduce an angle between the first and third bones; wherein
at least one of the first and third fasteners is cannulated and configured to be secured in a bore in at least one of the first bone and third bone, respectively; and wherein
the elongate flexible member is configured to pass through a cannulation of at least one of the first and third fasteners.

2. The apparatus according to claim 1, wherein the first bone is a first metatarsal bone, the second bone is a first proximal phalanx, and the third bone is a second metatarsal bone, and the fibrous membrane is adapted to span the joint between the first proximal phalanx and the first metatarsal on the medial side.

3. The apparatus according to claim 2, wherein the elongate flexible member is configured to pass through a cannulation of the first fastener, which is secured in a bore in the first metatarsal bone.

4. A surgical method, comprising:
securing a proximal arm of a stretchable elastic fibrous membrane to a first bone;
securing a distal arm of the fibrous membrane to a second bone, and
stretching the fibrous membrane so as to align the second bone relative to the first bone; and
fastening an elongate flexible member to the first bone with a first fastener and to a third bone, adjacent to the first bone, with a third fastener so as to reduce an angle between the first and third bones; wherein
at least one of the first and third fasteners is cannulated and configured to be secured in a bore in at least one of the first bone and third bone, respectively; wherein the elongate flexible member is configured to pass through a cannulation of at least one of the first and third fasteners.

5. The method according to claim 4, wherein the first bone is a first metatarsal bone, the second bone is a first proximal phalanx, the third bone is a second metatarsal, and the fibrous membrane spans a medial side of a joint between the first metatarsal bone and the first proximal phalanx.

* * * * *